(12) United States Patent
During

(10) Patent No.: US 10,195,165 B2
(45) Date of Patent: *Feb. 5, 2019

(54) METHODS OF TREATING PRADER-WILLI SYNDROME

(71) Applicant: Ovid Therapeutics Inc., New York, NY (US)

(72) Inventor: Matthew During, Weston, CT (US)

(73) Assignee: OVID THERAPEUTICS INC., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/682,967

(22) Filed: Aug. 22, 2017

(65) Prior Publication Data
US 2017/0348255 A1  Dec. 7, 2017

Related U.S. Application Data

(63) Continuation of application No. 15/142,826, filed on Apr. 29, 2016, now abandoned.

(60) Provisional application No. 62/154,875, filed on Apr. 30, 2015.

(51) Int. Cl.
*A61K 31/145* (2006.01)
(52) U.S. Cl.
CPC .................................. *A61K 31/145* (2013.01)
(58) Field of Classification Search
CPC .................................................. A61K 31/145
See application file for complete search history.

(56) References Cited

U.S. PATENT DOCUMENTS

| | | | |
|---|---|---|---|
| 2,830,083 A | 4/1958 | Gilbert et al. | |
| 3,947,579 A | 3/1976 | Fuxe | |
| 4,084,000 A | 4/1978 | Fuxe | |
| 4,129,652 A | 12/1978 | Fuxe | |
| 4,138,484 A | 2/1979 | Fuxe | |
| 8,461,389 B2 | 6/2013 | Regan et al. | |
| 9,610,261 B2 | 4/2017 | During | |
| 2010/0016425 A1 | 1/2010 | Vath | |
| 2011/0034562 A1 | 2/2011 | Regan | |
| 2011/0172188 A1 | 7/2011 | Mouthon et al. | |

FOREIGN PATENT DOCUMENTS

WO    2011/147889 A1    12/2011

OTHER PUBLICATIONS

Sams-Dodd (Drug discovery today, vol. 10, No. 2, 2005, pp. 139-147 ).
Cassidy (European journal of Human genetics, 2009, (17), pp. 3-13) i.
Horig et al. Journal of Translational Medicine 2004, 2(44).
Low, et al., "Suvren in Brain-Injuured Children", The Journal of Pediatrics, vol. 52, No. 3: pp. 259-263; Mar. 1958.
Dobkin, A. B., "Efficacy of Ataractic Drugs in Clinical Anaesthesia: A review", Canadian Anaesthesiology Society Journal, vol. 5, No. 2, pp. 177-208; Apr. 1958.
Kopf et al., "Pharmacology and Toxicology of Captodiamine (p-Butyl-mercapto-benzhydryl-?-dimethylamino-ethylsulphide)", Pharmacological and Biological Research Laboratories II, Lundbeck & Co., AIS, Copenhagen, Arzneimittel Forschung Drug Research,pp. 154-159; 1958.
Mercier-Guyon et al., "Comparative Study of the Effects of Captodiamine and Lorazepam on Car Driving Ability", Clinical Pharmacodynamics, vol. 17, No. 6, pp. 451-459; Jun. 1999.
Mercier-Guyon et al., Brief Report—"The Role of Captodiamine in the Withdrawal From Long-Term Benzodiazepine Treatment", Current Medical Research and Opinion, vol. 20, No. 9, Paper 2532, pp. 1347-1355; 2004.
Ring and Regan, "Captodiamine, a Putative Antidepressant, Enhances Hypothalamic BDNF Expression in Vivo by Synergistic 5-HT2c Receptor Antagonism and Sigma-1 Receptor Agonism", Journal of Psychopharmacology, vol. 27, No. 10, pp. 930-939; 2013.
Du et al., "Is Dysregulation of the HPA-Axis a Core Pathophysiology Mediating Co-Morbid Depression in Neurodegenerative Diseases?" Frontiers in Psychiatry, vol. 6, Article 32, pp. 1-33; Mar. 2015.
Aycan et al., "Prader-Willi Syndrome and Growth Hormone Deficiency", Journal of Clinical Research in Pediatric Endocrinology, vol. 6, No. 2, pp. 62-67; 2014.

(Continued)

*Primary Examiner* — Savitha M Rao
(74) *Attorney, Agent, or Firm* — Carter, Deluca, Farrell & Schmidt, LLP

(57) ABSTRACT

Methods of treating Prader-Willi syndrome in a subject in need of treatment are provided. The methods include administering to the subject an effective amount of a compound of Formula I,

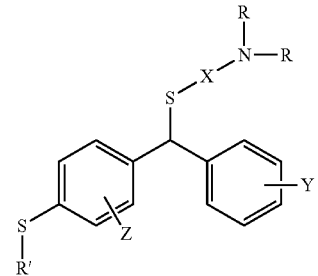

or a pharmaceutically acceptable salt thereof, wherein R, R', X, Y and Z are defined as set forth in the specification. In embodiments, an effective amount of captodiamine or a pharmaceutically acceptable salt thereof is administered to the subject.

10 Claims, No Drawings

(56) References Cited

OTHER PUBLICATIONS

Cao et al., "Molecular Therapy of Obesity and Diabetes Using a Physiological Autoregulatory Approach", National Institute of Health, National Medicine, vol. 15, No. 4, pp. 447-454 (pp. 1-16); Jan. 23, 2014.
International Search Report and Written Opinion of the International Searching Authority, dated Aug. 4, 2016, corresponding to International Application No. PCT/US16/30188; 11 total pages.

METHODS OF TREATING PRADER-WILLI SYNDROME

CROSS-REFERENCE TO RELATED APPLICATION

This application claims the benefit of, and priority to, U.S. patent application Ser. No. 15/142,826, filed Apr. 29, 2016, which claims priority to U.S. Provisional Patent Application No. 62/154,875 filed on Apr. 30, 2015, the entire contents of each of which are incorporated by reference herein.

TECHNICAL FIELD

Methods of treating Prader-Willi Syndrome.

BACKGROUND

Prader-Willi syndrome (PWS) is a genetic disease caused by lack of expression of genes from an imprinted region of the paternally inherited chromosome 15q11-q13, near the centromere (Aycan and Bas, *J Clin Res Pediatr Endocrinol*, 6(2):62-67 (2014)). The frequency of the disease is between about 1/10,000 and 1/30,000 with approximately 400,000 PWS patients living worldwide. PWS is a spectrum disorder which affects many systems in the body. Subjects with PWS typically suffer from a host of symptoms including neurologic, cognitive, endocrine, and behavioral abnormalities. Initially, infants exhibit hypotonia (floppy baby syndrome) and experience difficulty in sucking and feeding which can lead to growth delay. Subjects with PWS frequently have poor muscle tone, growth hormone deficiency, low levels of sex hormones, a constant feeling of hunger and excessive appetite (hyperphagia). They overeat, leading to weight gain, obesity and a high incidence of diabetes. Other signs appear including short stature, poor motor skills, underdeveloped sex organs, and mild intellectual and learning disabilities. PWS subjects may experience delayed speech and language development, and infertility. Behavioral symptoms may include cognitive impairment, cognitive rigidity, emotional lability and obsessive-compulsive behavior, with autistic symptomology, psychotic episodes, and biopolar disorder with psychosis. Additional clinical manifestations may include excessive daytime sleepiness, scoliosis, osteopenia/osteoporosis, decreased gastrointestinal motility, sleep disturbances, and reduced pain sensitivity.

PWS is the most common genetic neurodevelopmental disorder associated with obesity. Data indicates that PWS is associated with an approximate 50% reduction in plasma BDNF levels normalized to body weight (Han et al., *J. Clin. Endo. Metab.*, 95,3532-36 (2010)). Studies also show that selectively up-regulating BDNF in the hypothalamus inhibits appetite and weight gain in mice on a high fat diet, and at very high levels of expression using viral vector gene transfer causes severe weight loss in normal control chow fed mice (Cao, et al., *Nat Med.*, 15(4):447-54 (2009)). BDNF appears to act downstream to other modulators of feeding, notably leptin and the MC4 receptor.

There is currently no cure for PWS. Growth hormone, exercise, and dietary supervision can help build muscle mass and control weight. Treatment with human growth hormone starting by 2 years of age has been reported to improve body composition, motor function, height, and lipid profiles. See, Carrel et al., *J Clin Endocrinol Metab* 95(3):1131-1136 (2010 March). Other treatments may include oxytocin, sex hormones and behavior therapy. However, most people with PWS will need specialized care and supervision throughout their lives. There remains a need for improved and/or additional therapies for treating PWS.

Captodiamine (also known as captodiame) (2-[(4-butyl-sulfanylphenyl)-phenyl-methyl]sulfanyl-N,N-dimethyl-ethanamine) was developed in the 1950's and is a derivative of the antihistamine diphenhydramine. Captodiamine was identified in a class of compounds designated as sedatives and antispasmodics. See, e.g., U.S. Pat. No. 2,830,083, incorporated herein by reference. It was subsequently developed for treatment of anxiety disorders and marketed as an anxiolytic. The drug is not a potent hypnotic and appeared to be safe and well tolerated. Although no formal double blind randomized studies were carried out on captodiamine when it was initially marketed, it was widely prescribed.

Captodiamine was marketed as SUVREN® by Ayerst at the time notwithstanding the fact that there was a paucity of published studies. In the early1960's the FDA DESI (Drug Evaluation & Safety Initiative) program was implemented, i.e., drugs which did not have compelling evidence of efficacy, strong proponents, or external champions, were essentially struck off the register, or removed from the approved list. Captodiamine was one such drug, and essentially disappeared.

In 1999, a comparative study on the effects of captodiamine and lorazepam on car driving ability was conducted (Mercier-Guyon, et al., *Clin Drug Invest*, 17 (6): 451-459 (1999)). Captodiamine, as compared to lorazepam, reportedly improved the concentration and dexterity of individuals when driving, without inducing a tendency to drowsiness. In another study, captodiamine treatment was associated with lower severity of benzodiazepine withdrawal symptoms as compared to placebo (Mercier-Guyon et al., *Curr Med Res Opin.*, 20(9):1347-1355 (2004)).

In 2013, a group from University College Dublin, published a paper in which they reported that captodiamine had activity as a sigma-1 receptor agonist as well as a 5-HT$_{2C}$ antagonist and dopamine D3 agonist (Ring and Regan, *Journal of Psychopharmacology*, 27(10):930-939 (2013)). Captodiamine was shown to increase brain-derived neurotrophic factor (BDNF) protein levels in the hypothalamus, but not in the cortex or the hippocampus. U.S. Pat. No. 8,461,389 describes use of captodiamine in the treatment of anxiety and/or depression associated with an affective disorder and/or symptoms associated with cognitive impairment disorder.

SUMMARY

Methods of treating Prader-Willi Syndrome are provided and, in embodiments, include administering to a subject in need thereof a pharmaceutical composition including an effective amount of a compound of Formula I,

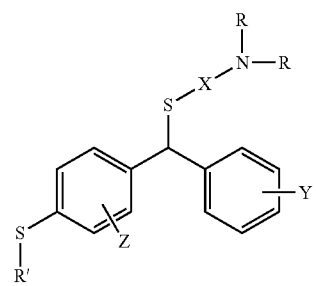

wherein X is an ethylene, propylene, butylene or pentylene group; R is $C_{1-9}$ alkyl, preferably $C_{1-5}$ alkyl; R' is $C_{1-9}$ alkyl, alkenyl or alkynyl; Y is hydrogen, halide such as chloro, fluoro, iodo or bromo, hydroxy$C_{1-4}$alkyl, amino, $C_{1-4}$alkylamino, acetylamino or thio; and Z is hydrogen, halide such as chloro, fluoro, iodo or bromo, hydroxy$C_{1-4}$ alkyl, amino, $C_{1-4}$ alkylamino, acetylamino or thio, or a pharmaceutically acceptable salt thereof.

In embodiments, X may be an ethylene, propylene, butylene, or pentylene group and R is methyl, R' is butyl, Y is hydrogen and Z is hydrogen; or R is $C_{1-9}$ alkyl, $C_{1-5}$ alkyl, and R' is butyl, X is ethylene, Y is hydrogen and Z is hydrogen.

In embodiments, Y may be hydrogen, halide such as chloro, fluoro, iodo or bromo, hydroxy$C_{1-4}$alkyl, amino, $C_{1-4}$alkylamino, acetylamino, thio and R is methyl, R' is butyl, X is ethylene and Z is hydrogen.

In embodiments, Z may be hydrogen, halide such as chloro, fluoro, iodo or bromo, hydroxy$C_{1-4}$alkyl, amino, $C_{1-4}$alkylamino, acetylamino, thio and R is methyl, R' is butyl, X is ethylene and Y is hydrogen.

In embodiments, R' may be $C_{1-9}$ alkyl, alkenyl or alkynyl and R is methyl, X is ethylene, Y is hydrogen and Z is hydrogen.

In embodiments, methods of treating Prader-Willi Syndrome include administering to a subject in need thereof a pharmaceutical composition including an effective amount of a compound of Formula II,

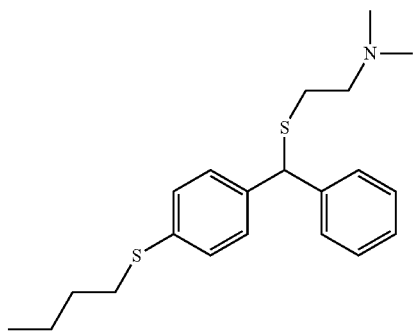

II also known as 2-[(4-butylsulfanylphenyl)-phenylmethyl]sulfanyl-N,N-dimethylethanamine (captodiamine), or a pharmaceutically acceptable salt thereof.

In embodiments, a composition including from 0.1 mg to 1500 mg of compound of Formula 1 or a pharmaceutically acceptable salt thereof is administered within a 24-hour period. In embodiments, a composition including a compound of Formula 1 or a pharmaceutically acceptable salt thereof is administered from one to four times a day. In embodiments, administering a composition including a compound of Formula I or a pharmaceutically acceptable salt thereof is accomplished via one or more of the following routes: oral, buccal, sublingual, rectal, topical, intranasal, vaginal, and parenteral. In embodiments, administering a composition including a compound of Formula I or a pharmaceutically acceptable salt thereof provides improvement in at least one of the following symptoms: hypotonia, difficulty in sucking, difficulty in feeding, poor muscle tone, growth hormone deficiency, low levels of sex hormones, a constant feeling of hunger, excessive appetite (hyperphagia), weight gain, obesity, short stature, poor motor skills, underdeveloped sex organs, intellectual disability, learning disability, delayed speech development, delayed language development, infertility, cognitive impairment, cognitive rigidity, emotional lability, self-injury, obsessive-compulsive behavior, autistic symptomology, psychotic episodes, bipolar disorder with psychosis, excessive daytime sleepiness, scoliosis, osteopenia/osteoporosis, decreased gastrointestinal motility, sleep disturbances, and/or reduced pain sensitivity.

In embodiments, the subject is administered a composition including 0.1 mg to 1500 mg of captodiamine or a pharmaceutically acceptable salt thereof. In embodiments, the subject is administered a composition including 1 mg to 500 mg of captodiamine or a pharmaceutically acceptable salt thereof. In embodiments, the subject is administered a composition including 50 mg to 250 mg of captodiamine or a pharmaceutically acceptable salt thereof. In embodiments, a composition including from 1 mg to 1500 mg of captodiamine or a pharmaceutically acceptable salt thereof is administered within a 24-hour period. In embodiments, the total amount of captodiamine or a pharmaceutically acceptable salt thereof administered to the subject in a twenty-four hour period is between 1 mg and 1500 mg. In embodiments, the total amount of captodiamine or a pharmaceutically acceptable salt thereof administered to the subject in a twenty-four hour period is between 1 mg and 500 mg. In embodiments, a composition including captodiamine or a pharmaceutically acceptable salt thereof is administered from one to four times a day.

In embodiments, administering a composition including captodiamine or a pharmaceutically acceptable salt thereof is accomplished via one or more of the following routes: oral, buccal, sublingual, rectal, topical, intranasal, and parenteral. In embodiments, administering a composition including captodiamine or a pharmaceutically acceptable salt thereof provides improvement in at least one of the following symptoms: hypotonia, difficulty in sucking, difficulty in feeding, poor muscle tone, growth hormone deficiency, low levels of sex hormones, a constant feeling of hunger, excessive appetite (hyperphagia), weight gain, obesity, short stature, poor motor skills, underdeveloped sex organs, intellectual disability, learning disability, delayed speech development, delayed language development, infertility, cognitive rigidity, emotional lability, obsessive-compulsive behavior, autistic symptomology, psychotic episodes, bipolar disorder with psychosis, excessive daytime sleepiness, scoliosis, osteopenia/osteoporosis, decreased gastrointestinal motility, sleep disturbances, and/or reduced pain sensitivity.

DETAILED DESCRIPTION

Described herein are methods and compositions for treating Prader-Willi syndrome by administering to a subject in need thereof a pharmaceutical composition including an effective amount of a compound of Formula I,

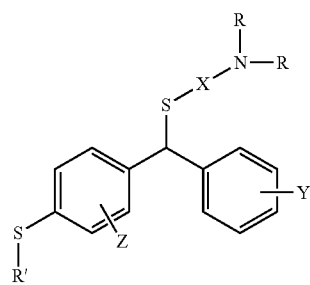

I wherein X is an ethylene, propylene, butylene or pentylene group; R is $C_{1-9}$ alkyl, preferably $C_{1-5}$ alkyl; R' is $C_{1-9}$ alkyl, alkenyl or alkynyl; Y is hydrogen, halide such as chloro, fluoro, iodo or bromo, hydroxy$C_{1-4}$alkyl, amino, $C_{1-4}$alkylamino, acetylamino or thio; and Z is hydrogen, halide such as chloro, fluoro, iodo or bromo, hydroxy$C_{1-4}$ alkyl, amino, $C_{1-4}$ alkylamino, acetylamino or thio, or a pharmaceutically acceptable salt thereof.

In embodiments, X may be an ethylene, propylene, butylene, or pentylene group and R is methyl, R' is butyl, Y is hydrogen and Z is hydrogen; or R is $C_{1-9}$ alkyl, $C_{1-5}$ alkyl, and R' is butyl, X is ethylene, Y is hydrogen and Z is hydrogen.

In embodiments, Y may be hydrogen, halide such as chloro, fluoro, iodo or bromo, hydroxy$C_{1-4}$alkyl, amino, $C_{1-4}$alkylamino, acetylamino, thio and R is methyl, R' is butyl, X is ethylene and Z is hydrogen.

In embodiments, Z may be hydrogen, halide such as chloro, fluoro, iodo or bromo, hydroxy$C_{1-4}$alkyl, amino, $C_{1-4}$alkylamino, acetylamino, thio and R is methyl, R' is butyl, X is ethylene and Y is hydrogen.

In embodiments, R' may be $C_{1-9}$ alkyl, alkenyl or alkynyl and R is methyl, X is ethylene, Y is hydrogen and Z is hydrogen.

In embodiments, methods and compositions for treating Prader-Willi Syndrome include administering to a subject in need thereof a pharmaceutical composition including an effective amount of a compound of Formula II,

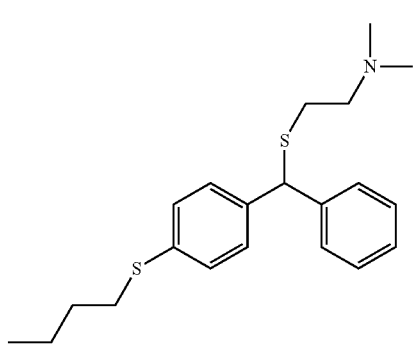

II also known as 2-[(4-butylsulfanylphenyl)-phenylmethyl]sulfanyl-N,N-dimethylethanamine (captodiamine), or a pharmaceutically acceptable salt thereof.

The chemical formula for captodiamine is $C_{21}H_{29}NS_2$ and its CAS number is 486-17-9. The compound is also known under the following synonyms: 2-[(p-(Butylthio)-alpha-phenylbenzyl)thio)-N,N-dimethylethylamine, 4-06-00-06672 (Beilstein Handbook Reference), 486-17-9, BRN 2625367, Captodiame, Captodiamin, Captodiamine, Captodiamo [INN-Spanish], Captodiamum [INN-Latin], Captodramin, Captodramine, Covatin, Covatix, EINECS 207-629-1, Ethanamine, 24(4-(butylthio)phenyl)phenylmethyl)thio)-N,N-dimethyl-(9CI), Ethanamine, 2-[[[4-(butylthio)phenyl]phenylmethyl]thio]-N,N-dimethyl-, ETHYLAMINE, 2-[(p-(BUTYLTHIO)-alpha-PHENYLBENZYL)THIO)-N,N-DIMETHYL-, Kaptodiamin [Czech], N 68, p-Butylmercaptobenzhydryl-beta-dimethylamino-ethyl sulphide, VUFB2350.

Symptoms of Prader-Willi syndrome include hypotonia, difficulty in sucking, difficulty in feeding, poor muscle tone, growth hormone deficiency, low levels of sex hormones, a constant feeling of hunger, excessive appetite (hyperphagia), weight gain, obesity, short stature, poor motor skills, underdeveloped sex organs, intellectual disability, learning disability, delayed speech development, delayed language development, infertility, cognitive rigidity, cognitive impairment, emotional lability, obsessive-compulsive behavior, autistic symptomology, excessive daytime sleepiness, scoliosis, osteopenia/osteoporosis, decreased gastrointestinal motility, sleep disturbances, and/or reduced pain sensitivity. In addition, in approximately 10% of individuals with PWS, more severe psychiatric illness can result including psychotic episodes, depression and bipolar disorder with psychosis.

Criteria regarding learning disorders are provided in the DSM-5 that considers specific learning disabilities to be a type of neurodevelopmental disorder that impedes the ability to learn or use specific academic skills (e.g., reading, writing, or arithmetic), which are the foundation for other learning.

Cognitive impairment may be measured against normal cognitive function, which refers to the normal physiologic activity of the brain, including, but not limited to, one or more of the following: mental stability, memory/recall abilities, problem solving abilities, reasoning abilities, thinking abilities, judging abilities, ability to discriminate or make choices, capacity for learning, ease of learning, perception, intuition, attention, and awareness, as measured by any criteria suitable in the art.

Cognitive impairment also includes deficits in mental activities that are mild or that otherwise do not significantly interfere with daily life. Mild cognitive impairment (MCI) is an example of such a condition. A patient with mild cognitive impairment may display symptoms of dementia (e.g., difficulties with language or memory) but the severity of these symptoms is such that a diagnosis of dementia may not be appropriate.

One skilled in the art will appreciate that there are numerous human and animal models that may be used to evaluate and compare the relative safety and efficacy of compounds according to Formula I such as captodiamine or pharmaceutically acceptable salts thereof for the treatment of cognitive impairment. In humans, cognitive function may be measured, for example and without limitation, by the clinical global impression of change scale (CGI); the Mini Mental State Exam (MMSE) (aka the Folstein Test); the Neuropsychiatric Inventory (NPI); the Clinical Dementia Rating Scale (CDR); the Cambridge Neuropsychological Test Automated Battery (CANTAB), the Sandoz Clinical Assessment-Geriatric (SCAG) scale, the Benton Visual Retention Test (BVRT), Montreal Cognitive Assessment (MoCA) or Digit Symbol Substitution Test (DSST).

In animal model systems, cognitive function may be measured in various conventional ways known in the art, including using a Morris Water Navigation Task, Barnes maze, radial arm maze task, T maze and the like. Other tests known in the art may also be used to assess cognitive function, such as novel object recognition and odor recognition tasks.

Cognitive function may also be measured using imaging techniques such as Positron Emission Tomography (PET), functional magnetic resonance imaging (fMRI), Single Photon Emission Computed Tomography (SPECT), or any other imaging technique that allows one to measure brain function. In animals, cognitive function may also be measured with electrophysiological techniques.

Accordingly, a compound of Formula I, such as captodiamine, or a pharmaceutically acceptable salt thereof is used to treat a subject having Prader-Willi syndrome. The subject may be an animal, e.g., mammal, e.g., human, etc. As used herein, the terms "treat", "treatment" or "treating" encompass any manner in which the symptoms or pathology of a condition, disorder or disease associated with Prader-Willi syndrome are ameliorated or otherwise beneficially altered. In embodiments, "treat", "treatment" or "treating" can refer to inhibiting a disease or condition, e.g., arresting or reducing its development or at least one clinical or subclinical symptom thereof. In embodiments, "treat", "treatment" or "treating" can refer to relieving the disease or condition, e.g., causing regression of the disease or condition or at least one of its clinical or subclinical symptoms. In embodiments, "treating cognitive impairment" means ameliorating, beneficially altering and/or providing relief from one or more of the symptoms of cognitive impairment. The benefit to a subject being treated may be statistically significant, mathematically significant, or at least perceptible to the subject and/or the physician.

In embodiments, the terms "effective amount" or "therapeutically effective amount" refer to an amount of a compound, material, composition, medicament, or other material that is effective to achieve a particular pharmacological and/or physiologic effect in connection with PWS symptoms such as, but not limited to, one or more of the following: reducing or eliminating difficulty in sucking, reducing or eliminating difficulty in feeding, reducing or eliminating poor muscle tone, reducing or eliminating growth hormone deficiency, increasing levels of sex hormones, reducing or eliminating a constant feeling of hunger, reducing or eliminating excessive appetite (hyperphagia), reducing or eliminating weight gain, reducing or eliminating obesity, reducing or eliminating short stature, increasing motor skills, reducing or eliminating underdeveloped sex organs, reducing or eliminating intellectual disability, reducing or eliminating learning disability, reducing or eliminating delayed speech development, reducing or eliminating delayed language development, reducing or eliminating infertility, reducing or eliminating cognitive rigidity, reducing or eliminating cognitive impairment, reducing or eliminating emotional lability, reducing or eliminating obsessive-compulsive behavior, reducing or eliminating autistic symptomology, reducing or eliminating psychotic episodes, reducing or eliminating bipolar disorder with psychosis, reducing or eliminating excessive daytime sleepiness, reducing or eliminating scoliosis, reducing or eliminating osteopenia/osteoporosis, reducing or eliminating decreased gastrointestinal motility, reducing or eliminating sleep disturbances, and/or reducing or eliminating reduced pain sensitivity, enhancing cognitive function, increasing daytime activity, improving learning (either the rate or ease of learning), improving attention, improving social behavior, and/or improving cerebrovascular function. In embodiments, effective amount refers to an amount which may be suitable to prevent a decline in any one or more of the above qualities, or, in embodiments, to improve any one or more of the above qualities, for example, constant feeling of hunger, excessive appetite (hyperphagia), weight gain, obesity, cognitive function or performance, learning rate or ability, problem solving ability, attention span and ability to focus on a task or problem, social behavior, and the like. In embodiments, an effective amount may be suitable to reduce either the extent or rate of decline in a subject's appetite dysregulation, weight loss, cognitive skills or functioning, and/or the effective amount may be suitable to delay the onset of such decline. In embodiments, an effective amount increases hypothalamic BDNF expression. Such effectiveness may be achieved, for example, by administering compositions described herein to an individual or to a population. In embodiments, the reduction, or delay of such a decline, or the improvement in an individual or population can be relative to a cohort, e.g., a control subject or a cohort population that has not received the treatment, or been administered the composition or medicament.

The dosage amount can vary according to a variety of factors such as subject-dependent variables (e.g., age, immune system, health, etc.), the disease or disorder being treated, as well as the route of administration and the pharmacokinetics of the agent being administered.

In embodiments, methods include treating PWS by administering to a patient in need thereof a pharmaceutical composition including about 0.01 mg to about 1000 mg of a compound of Formula I, such as captodiamine, or a pharmaceutically acceptable salt thereof. In embodiments, doses may be, e.g., in the range of about 0.1 to 1500 mg, 0.1 to 1250 mg, 0.1 to 1000 mg, 0.1 to 750 mg, 0.1 to 500 mg, 0.1 to 450 mg, 0.1 to 300 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 1 mg, 1 to 1500 mg, 1 to 1000 mg, 1 to 500 mg, 1 to 300 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 1 to 25 mg, 1 to 20 mg, 1 to 15 mg, 1 to 10 mg, 1 to 5 mg, 5 to 1500 mg, 5 to 1000 mg, 5 to 500 mg, 5 to 300 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 10 to 1500 mg, 10 to 1000 mg, 10 to 500 mg, 10 to 300 mg, 10 to 250 mg, 10 to 200 mg, 10 to 175 mg, 10 to 150 mg, 10 to 125 mg, 10 to 100 mg, 10 to 75 mg, 10 to 50 mg, 10 to 30 mg, 10 to 25 mg, 10 to 20 mg, 10 to 15 mg, 15 to 1500 mg, 15 to 1000 mg, 15 to 500 mg, 15 to 300 mg, 15 to 250 mg, 15 to 200 mg, 15 to 175 mg, 15 to 150 mg, 15 to 125 mg, 15 to 100 mg, 15 to 75 mg, 15 to 50 mg, 15 to 30 mg, 15 to 25 mg, 15 to 20 mg, 20 to 1500 mg, 20 to 1000 mg, 20 to 500 mg, 20 to 300 mg, 20 to 250 mg, 20 to 200 mg, 20 to 175 mg, 20 to 150 mg, 20 to 125 mg, 20 to 100 mg, 20 to 75 mg, 20 to 50 mg, 20 to 30 mg, 20 to 25 mg, 25 to 1500 mg, 25 to 1000 mg, 25 to 500 mg, 25 to 300 mg, 25 to 250 mg, 25 to 200 mg, 25 to 175 mg, 25 to 150 mg, 25 to 125 mg, 25 to 100 mg, 25 to 75 mg, 25 to 50 mg, 25 to 30 mg, 30 to 1500 mg, 30 to 1000 mg, 30 to 500 mg, 30 to 300 mg, 30 to 250 mg, 30 to 200 mg, 30 to 175 mg, 30 to 150 mg, 30 to 125 mg, 30 to 100 mg, 30 to 75 mg, 30 to 50 mg, 35 to 1500 mg, 35 to 1000 mg, 35 to 500 mg, 35 to 300 mg, 35 to 250 mg, 35 to 200 mg, 35 to 175 mg, 35 to 150 mg, 35 to 125 mg, 35 to 100 mg, 35 to 75 mg, 35 to 50 mg, 40 to 1500 mg, 40 to 1000 mg, 40 to 500 mg, 40 to 300 mg, 40 to 250 mg, 40 to 200 mg, 40 to 175 mg, 40 to 150 mg, 40 to 125 mg, 40 to 100 mg, 40 to 75 mg, 40 to 50 mg, 50 to 1500 mg, 50 to 1000 mg, 50 to 500 mg, 50 to 300 mg, 50 to 250 mg, 50 to 200 mg, 50 to 175 mg, 50 to 150 mg, 50 to 125 mg, 50 to 100 mg, 50 to 75 mg, 75 to 1500 mg, 75 to 1000 mg, 75 to 500 mg, 75 to 300 mg, 75 to 250 mg, 75 to 200 mg, 75 to 175 mg, 75 to 150 mg, 75 to 125 mg, 75 to 100 mg, 100 to 1500 mg, 100 to 1000 mg, 100 to 500 mg, 100 to 300 mg, 100 to 250 mg, 100 to 200 mg, 100 to 175 mg, 100 to 150 mg, 100 to 125 mg, 125 to 1500 mg, 125 to 1000 mg, 125 to 500 mg, 125 to 300 mg, 125 to 250 mg, 125 to 200 mg, 125 to 175 mg, 125 to 150 mg, 150 to 1500 mg, 150 to 1000 mg, 150 to 500 mg, 150 to 300 mg, 150 to 250 mg, 150 to 200 mg, 150 to 175 mg, 175 to 1500 mg, 175 to 1000 mg, 175 to 500 mg, 175 to 300 mg, 175 to 250 mg, 175 to 200 mg, 200 to 1500 mg, 200 to 1000 mg, 200 to 500 mg, 200 to 300 mg, 200 to 250 mg, 250 to 1500 mg, 250 to 1000 mg, 250 to 500 mg, 250 to 300 mg, 7.5 to 15 mg, 2.5 to 5 mg, 1 to 5 mg, with doses of, e.g., about 0.25 mg, 0.5 mg, 0.75 mg, 1 mg, 1.25 mg, 1.5 mg, 1.75 mg, 2.0 mg, 2.5 mg, 3.0 mg, 3.5 mg, 4.0 mg, 4.5 mg, 5 mg, 10 mg, 15 mg, 20 mg, 25 mg, 30, mg, 35 mg, 40 mg, 45 mg, 50 mg, 75 mg, 100 mg, 125 mg, 150 mg, 175 mg, 200 mg, 225 mg, 250 mg, 275 mg, 300 mg, 400 mg and 500 mg being examples.

In embodiments, pharmaceutical compositions may include a compound of Formula I, such as captodiamine, or a pharmaceutically acceptable salt thereof in an amount of, e.g., about 0.01 to 500 mg, 0.1 to 500 mg, 0.1 to 450 mg, 0.1 to 300 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 1 mg, 0.5 to 500 mg, 0.5 to 450 mg, 0.5 to 300 mg, 0.5 to 250 mg, 0.5 to 200 mg, 0.5 to 175 mg, 0.5 to 150 mg, 0.5 to 125 mg, 0.5 to 100 mg, 0.5 to 75 mg, 0.5 to 50 mg, 0.5 to 30 mg, 0.5 to 25 mg, 0.5 to 20 mg, 0.5 to 15 mg, 0.5 to 10 mg, 0.5 to 5 mg, 0.5 to 1mg, 1 to 500 mg, 1 to 450 mg, 1 to 300 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 1 to 25 mg, 1 to 20 mg, 1 to 15 mg, 1 to 10 mg, 1 to 5 mg, 5 to 500 mg, 5 to 450 mg, 5 to 300 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 10 to 500 mg, 10 to 450 mg, 10 to 300 mg, 10 to 250 mg, 10 to 200 mg, 10 to 175 mg, 10 to 150 mg, 10 to 125 mg, 10 to 100 mg, 10 to 75 mg, 10 to 50 mg, 10 to 30 mg, 10 to 25 mg, 10 to 20 mg, 10 to 15 mg, 15 to 500 mg, 15 to 450 mg, 15 to 300 mg, 15 to 250 mg, 15 to 200 mg, 15 to 175 mg, 15 to 150 mg, 15 to 125 mg, 15 to 100 mg, 15 to 75 mg, 15 to 50 mg, 15 to 30 mg, 15 to 25 mg, 15 to 20 mg, 20 to 500 mg, 20 to 450 mg, 20 to 300 mg, 20 to 250 mg, 20 to 200 mg, 20 to 175 mg, 20 to 150 mg, 20 to 125 mg, 20 to 100 mg, 20 to 75 mg, 20 to 50 mg, 20 to 30 mg, 20 to 25 mg, 25 to 500 mg, 25 to 450 mg, 25 to 300 mg, 25 to 250 mg, 25 to 200 mg, 25 to 175 mg, 25 to 150 mg, 25 to 125 mg, 25 to 100 mg, 25 to 75 mg, 25 to 50 mg, 25 to 30 mg, 30 to 500 mg, 30 to 450 mg, 30 to 300 mg, 30 to 250 mg, 30 to 200 mg, 30 to 175 mg, 30 to 150 mg, 30 to 125 mg, 30 to 100 mg, 30 to 75 mg, 30 to 50 mg, 40 to 500 mg, 40 to 450 mg, 40 to 400 mg, 40 to 250 mg, 40 to 200 mg, 40 to 175 mg, 40 to 150 mg, 40 to 125 mg, 40 to 100 mg, 40 to 75 mg, 40 to 50 mg, 50 to 500 mg, 50 to 450 mg, 50 to 300 mg, 50 to 250 mg, 50 to 200 mg, 50 to 175 mg, 50 to 150 mg, 50 to 125 mg, 50 to 100 mg, 50 to 75 mg, 75 to 500 mg, 75 to 450 mg, 75 to 300 mg, 75 to 250 mg, 75 to 200 mg, 75 to 175 mg, 75 to 150 mg, 75 to 125 mg, 75 to 100 mg, 100 to 500 mg, 100 to 450 mg, 100 to 300 mg, 100 to 250 mg, 100 to 200 mg, 100 to 175 mg, 100 to 150 mg, 100 to 125 mg, 125 to 500 mg, 125 to 450 mg, 125 to 300 mg, 125 to 250 mg, 125 to 200 mg, 125 to 175 mg, 125 to 150 mg, 150 to 500 mg, 150 to 450 mg, 150 to 300 mg, 150 to 250 mg, 150 to 200 mg, 200 to 500 mg, 200 to 450 mg, 200 to 300 mg, 200 to 250 mg, 250 to 500 mg, 250 to 450 mg, 250 to 300 mg, 300 to 500 mg, 300 to 450 mg, 300 to 400 mg, 300 to 350 mg, 350 to 500 mg, 350 to 450 mg, 350 to 400 mg, 400 to 500 mg, 400 to 450 mg, with 0.1 mg, 0.25 mg, 0.5 mg, 0.75 mg, 1 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg 175 mg, 200 mg, 225 mg, 250 mg, 275 mg, 300 mg, 325 mg, 350 mg, 375 mg, 400 mg, 425 mg, 450 mg, 475 mg, and 500 mg being examples.

Typically, dosages may be administered to a subject once, twice, three or four times daily, every other day, once weekly, or once a month. In embodiments, a compound of Formula I, such as captodiamine, or a pharmaceutically acceptable salt thereof is administered to a subject three times a day (e.g., at breakfast, lunch, and dinner), at a dose of 50 mg/administration (e.g., 150 mg/day). In embodiments, a compound of Formula I, such as captodiamine, or a pharmaceutically acceptable salt thereof is administered to a subject 250 mg/per day in one or more doses.

In embodiments, the dosage of a compound of Formula I, such as captodiamine, or a pharmaceutically acceptable salt thereof is 0.01-100 mg/kg, 0.5-50 mg/kg, 0.5-10 mg/kg or 25-50 mg/kg once, twice, three times or four times daily. For example, in embodiments, the dosage is 0.5 mg/kg, 1 mg/kg, 5 mg/kg, 7.5 mg/kg, or 10 mg/kg once, twice, three times or four times daily. In embodiments, a subject is administered a total daily dose of 0.01 mg to 1500 mg of a compound of Formula I, such as captodiamine, or a pharmaceutically acceptable salt thereof once, twice, three times, four times daily. In embodiments, the total amount administered to a subject in 24-hour period is, e.g., 1 mg, 5 mg, 10 mg, 25 mg, 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, or 500 mg. In embodiments, the subject may be started at a low dose and the dosage is escalated.

Suitable dosage forms for of a compound of Formula I, such as captodiamine, or a pharmaceutically acceptable salt thereof include, but are not limited to oral forms, such as tablets, hard or soft gelatin capsules, powders, granules and oral solutions, syrups or suspensions, troches, as well as the sublingual, buccal, intratracheal, intraocular, intranasal forms, forms adapted to inhalation, topical, transdermal, rectal forms such as suppositories, and implants for release of medication, parenteral forms, for example, intravenous, intra-arterial, intraperitoneal, intrathecal, intraventricular, intraurethrally, intrasternal, intracranial, intramuscularly or subcutaneously. In embodiments, for such parenteral administration, it may be in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

Pharmaceutical compositions herein may be provided with immediate release, delayed release, extended release, or modified release profiles. In embodiments, a delayed release dosage form is one that releases a drug (or drugs) at a time other than promptly after administration. In embodiments, an extended release dosage form is one that allows at least a twofold reduction in dosing frequency as compared to that drug presented as a conventional dosage form (e.g. as a solution or prompt drug-releasing, conventional solid dosage form). In embodiments, a modified release dosage form is one for which the drug release characteristics of time course and/or location are chosen to accomplish therapeutic or convenience objectives not offered by conventional dosage forms such as solutions, ointments, or promptly dissolving dosage forms. Delayed release and extended release dosage forms and their combinations may be considered as types of modified release dosage forms.

In embodiments, pharmaceutical compositions with different drug release profiles may be combined to create a two-phase or three-phase release profile. For example, pharmaceutical compositions may be provided with an immediate release and an extended release profile. In embodiments, pharmaceutical compositions may be provided with an extended release and delayed release profile. Such composition may be provided as pulsatile formulations, multilayer tablets, or capsules containing tablets, beads, granules, etc. Compositions may be prepared using a pharmaceutically acceptable "carrier" composed of materials that are considered safe and effective. The "carrier" includes all components present in the pharmaceutical formulation other than the active ingredient or ingredients. The term "carrier" includes, but is not limited to, diluents, binders, lubricants, glidants, disintegrants, fillers, and coating compositions.

As used herein, the term "pharmaceutically acceptable" refers to molecular entities and compositions that are "generally regarded as safe", e.g., that are physiologically tolerable and do not typically produce an allergic or similar untoward reaction when administered to a human. In embodiments, this term refers to molecular entities and compositions approved by a regulatory agency of the federal or a state government, as the GRAS list under section 204(s) and 409 of the Federal Food, Drug and Cosmetic Act, that is subject to premarket review and approval by the FDA or similar lists, the U.S. Pharmacopeia or another generally recognized pharmacopeia for use in animals, and more particularly in humans.

As used herein, the term "pharmaceutically acceptable salts" includes acid addition salts, addition salts of free bases, wherein the compound is modified by making acid or base salts thereof. Examples of pharmaceutically acceptable salts include but are not limited to mineral or organic acid salts of basic residues such as amines, and alkali or organic salts of acidic residues such as carboxylic acids. Pharmaceutically acceptable salts include conventional non-toxic salts or quaternary ammonium salts of the parent compound formed, for example, from non-toxic inorganic or organic acids. Such conventional non-toxic salts include those derived from inorganic acids such as hydrochloric, hydrobromic, sulfuric, sulfamic, phosphoric, and nitric acids; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, tolunesulfonic, naphthalenesulfonic, methanesulfonic, ethane disulfonic, and oxalic salts. In embodiments, eplivanserin or pharmaceutically acceptable salts may include a hemifumarate salt. The pharmaceutically acceptable salts of a compound of Formula I, such as captodiamine, can be synthesized from the parent compound, which contains a basic or acidic moiety, by conventional chemical methods.

The terms "about" or "approximately" as used herein mean within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, a range up to 10%, a range up to 5%, and/or a range up to 1% of a given value. Alternatively, particularly with respect to biological systems or processes, the term can mean within an order of magnitude, e.g., within 5-fold, or within 2-fold, of a value. "About" and "approximately" are used interchangeably herein.

The compounds of Formula I or Formula II may be racemic compounds of Formula I or II and/or optically active isomers thereof. In this regard, some of the compounds of Formula I and the compound of Formula II can have asymmetric carbon atoms, and therefore, can exist either as racemic mixtures or as individual optical isomers (enantiomers). Compounds described herein that contain a chiral center include all possible stereoisomers of the compound, including compositions including the racemic mixture of the two enantiomers, as well as compositions including each enantiomer individually, substantially free of the other enantiomer. Thus, for example, contemplated herein is a composition including the S enantiomer of a compound substantially free of the R enantiomer, or the R enantiomer substantially free of the S enantiomer. If the named compound includes more than one chiral center, the scope of the present disclosure also includes compositions including mixtures of varying proportions between the diastereomers, as well as compositions including one or more diastereomers substantially free of one or more of the other diastereomers. By "substantially free" it is meant that the composition includes less than 25%, 15%, 10%, 8%, 5%, 3%, or less than 1% of the minor enantiomer or diastereomer(s).

Methods for synthesizing, isolating, preparing, and administering various stereoisomers are known in the art. Separation of diastereoisomers or cis and trans isomers may be achieved by conventional techniques, such as, for example, by fractional crystallisation, chromatography or High Performance Liquid Chromatography (HPLC) of a stereoisomeric mixture of the agent or a suitable salt or derivative thereof. An individual enantiomer of a compound of Formula I, such as captodiamine, may also be prepared from a corresponding optically pure intermediate or by resolution, such as by HPLC of the corresponding racemate using a suitable chiral support or by fractional crystallisation of the diastereoisomeric salts formed by reaction of the corresponding racemate with a suitable optically active acid or base, as appropriate.

The following examples are included to augment the disclosure herein and should not be construed as limiting in any sense.

EXAMPLES

Example 1

Assessment of Effects of Captodiamine

This study, conducted by Mercier-Guyon, et al., supra, was a controlled, randomized, double-blind trial of captodiamine versus placebo conducted in 81 subjects presenting mild to moderate anxiety and treated for at least 6 months with a stable dose of benzodiazepine. The mean age of the included subjects was 40.5 years and men and women were equally represented. The study lasted ten weeks, including six weeks experimental treatment, divided into four phases. The first phase lasted 15 days, the second phase lasted 15 days, the third phase lasted 30 days and the fourth phase lasted 15 days. During the study, each subject was gradually weaned from benzodiazepines over a 14 day period using a tapering dose schedule and received captodiamine (150 mg/d) or placebo for 45 days from the beginning of the weaning period. The first phase, i.e., a run-in period, started with the screening visit when entry criteria were verified and informed consent was obtained. During the run-in period, no modification of drug treatment was made. At the end of this period, subjects were randomized either to placebo or captodiamine and treatment initiated for the following six weeks. Captodiamine was given as three 50 mg tablets per day. During the following two weeks (the second phase, i.e., weaning phase, designated as starting at D0), each subject was individually weaned from benzodiazepine treatment, reducing benzodiazepines consumption to zero within this time, and a minimum regimen proposed, with half the dose being given during the first week followed by a quarter of the dose for the second week and then discontinuation at D14 of the second phase. During the third phase (assessment phase), subjects continued captodiamine or placebo treatment in the absence of benzodiazepines. From the assessment visit at the end of the assessment phase until the final study visit at the end of the fourth phase (post-treatment phase), all treatment was discontinued. Outcome assessments were made at D0, D15, D21, D45 and D 60. The primary outcome criterion was the extent of withdrawal symptoms over the treatment period as assessed with the Tyrer Benzodiazepine Withdrawal Symptom Questionnaire (BWSQ).

During the two week weaning phase when benzodiazepines were discontinued, withdrawal symptoms emerged in both treatment groups. Analysis of the primary outcome criterion, the Tyrer BWSQ score, revealed a statistically significant difference ($p<0.0001$; ANCOVA with repeated measures) between the two study groups in favor of captodiamine attesting to a decrease in the number and intensity of withdrawal symptoms. For the anxiety scale, the self-reported anxiety scores rose in the placebo group during the weaning and assessment phases before returning to baseline at the end of the post-treatment period. In contrast, in the captodiamine treatment group, anxiety scores evolved little during the weaning phase and then fell during the assessment phase. There was a significant difference in scores between the two treatment groups at all observation points during the experimental phases of the study. For the drowsiness score, the scores for the placebo group remained stable during the weaning phase and then declined slightly, whereas they declined from D0 for the captodiamine group. Again, all inter-group differences were statistically significant during the experimental phases of the study. Once captodiamine treatment was stopped after 45 days, there was no re-emergence of anxiety or evidence for withdrawal symptoms.

Example 2

Experimental Protocol for Behavioral Evaluation of Captodiamine

This excerpted study, more fully reported in U.S. Pat. No. 8,461,389, involved three separate cohorts of C57B16 mice that were employed in the behavioral evaluation of captodiamine.

Materials and Methods I

Cohort 1 was used to evaluate the drug effect on prepulse inhibition, spatial learning, open-field and novel object recognition. Cohort 2 was used to evaluate drug effects on the forced swim test and the elevated X-maze. The behavioral tests were administered in sequence as per day number. The drug was administered by the intraperitoneal route and on the day of training the drug was administered after the behavioral analysis. Cohort 3 was used for analysis of growth factor (GF) expression (such as, for example, Brain Derived Neurotrophic Factor (BDNF and Glial Derived Neurotrophic Factor (GDNF). Captodiamine/UCD-0620 was administered at doses of 3 and 5 mg/kg. The compound was administered once daily, via the intraperitoneal route, for 7 days prior to testing and the animals were drug-free at time of training.

Materials and Methods II

The influence of captodiamine on open-field behavior, novel object recognition, forced swim test and water maze spatial learning. Captodiamine was administered by the intraperitoneal route at the doses indicated. Values were analyzed using a two way ANOVA and Student t-test and those with a p values<0.05 were accepted as significant and where appropriate are indicated with an asterisk.

Materials and Methods III

Analysis of receptor affinities was performed by Novascreen™ and those displacing >20% of the natural ligand are indicated by the filled boxes. Blood levels of captodiamine were determined by GC mass spectroscopy. In separate samples taken from a cannulated jugular at increasing time intervals following a single intraperitoneal injection of the drug (5 mg/kg). Growth factor analysis was performed using tissue homogenates and ELISA assays specific for each growth factor (Promega). Values were analyzed using a Student t-test and those with a p value<0.05 were accepted as significant.

Discussion of Results I and II

Captodiamine had no influence on basal locomotion in the open-field paradigm. However, animals tended to spend significantly more time in the center of the center of the arena, suggesting that captodiamine exerts an anxiolytic action. This anxiolytic action was confirmed using the elevated X-maze in which the treated animal spent a significantly longer periods exploring the open arms of the maze. Captodiamine exhibited no effect on the pre-pulse inhibition paradigm clearly demonstrating it to have little or no effect on mechanisms of sensory processing. In contrast, captodiamine treated animals, at the 3 mg/kg dose, spent significantly longer investigating objects during the training phase, as measured by the one-tailed t-test in the Novel Object Recognition Task. Captodiamine was also further differentiated by its significant pro-cognitive action in the water maze spatial learning task. The marked anxiolytic action of captodiamine also prompted a determination of its potential as an antidepressant. This action was confirmed by the significant increase on time to immobility that was observed in the forced swim test. The combined effect of captodiamine on open-field behavior and performance in the elevated X-maze suggests it to have anxiolytic actions that most likely contribute to its procognitive actions in water maze spatial paradigm and antidepressant actions in the forced swim test.

Results III—Receptor Affinity and Pharmacokinetics for Captodiamine

Affinities were determined by allowing a 1 μM concentration of captodiamine compete for receptor binding with a reference ligand (a compound with a known affinity for the receptor in question). The amount of reference ligand that is prevented from binding to a particular receptor is measured and this gives rise to the "percent target inhibition" value. The higher the target inhibition value, the greater the affinity captodiamine has for this particular receptor as it displaces a greater proportion of the reference ligand. This assay is an automated high throughput assay performed on cell lines that express only one type of receptor and was carried out by Novascreen (www.novascreen.com). Receptor affinity is a good starting point for determining the mechanism of action for a particular compound. In this case a greater than 90% inhibition value for the Sigma 1 receptor and the greater than 80% inhibition value for the dopamine D3 and serotonin 5HT$_{2c}$ receptor would suggest that the effects of captodiamine are predominantly mediated through these receptors. In contrast, captodiamine only demonstrates a greater than 20% inhibition value for the Sigma 2 receptor. Both the dopamine D3 receptor and the 5HT$_{2c}$ receptor show a greater than 80% inhibition value, demonstrating that some of the effects of captodiamine are mediated through these receptors.

Growth Factor Modulation

Captodiamine has no effect on Brain Derived Neurotrophic Factor (BDNF) expression levels and/or activity in either the prefrontal cortex or the hippocampus. However, captodiamine significantly increased the levels of expression of BDNF in the hypothalamus part of the brain. In contrast, captodiamine significantly decreased levels of expression of GDNF in the prefrontal cortex of the brain but not in either the hippocampus or the hypothalamus. The mechanism by which sigma-1 receptors modulate GDNF levels remains to be determined.

Example 3

Prospective Assessment of the Safety and Efficacy of Captodiamine in Ghrelin Suppression in Individuals with Prader-Willi Syndrome The purpose of this study is to evaluate the effect of captodiamine on levels of ghrelin, hunger, and body weight in people with Prader-Willi syndrome. This study will be a multi-center, randomized, placebo-controlled, double blind trial in which patients meeting entrance criteria will be randomly assigned to receive placebo or active drug. Enrolled subjects will have diagnosis of PWS confirmed by chromosome analysis (i.e. interstitial deletion of paternally-derived chromosome 15Q, uniparental maternal disomy or other chromosome 15 abnormalities), be 18 years and older, and have free T4, TSH values in the normal range (with or without thyroxine replacement). Subjects with confirmed hypogonadism who are corrected with adequate doses of sex steroid replacement, will have been treated for at least 6 months prior to entry and have no change in dosages over the study period. Patients with confirmed growth hormone deficiency who are corrected with adequate doses of replacement, will have been treated for at least 6 months prior to entry and have no change in dosages over the study period.

After baseline tests, subjects will be administered captodiamine or placebo for 6 months. At the end of this initial 6-month treatment period and a 4-month washout period, study subjects will then crossover to receive the alternative therapy (placebo or captodiamine) for an additional 6 months. Subjects will be followed for 16 months total at scheduled visits: 0, 2, 6, 10, 12, and 16 months. During each of these visits, testing will include measuring how well glucose (sugar) is processed, how much energy is burned off as heat, their amount of body fat, levels of the hormone ghrelin, and how much food is eaten at a meal. During these study periods participants will return monthly for physical examination and blood draw to check liver enzymes. Primary outcome measures are ghrelin levels (change from baseline to 6 months), appetite (change from baseline to 6 months), and body weight (change from baseline to 6 months). Secondary outcome measures are hormone levels (change from baseline to 6 months), body composition (change from baseline to 6 months), energy expenditure (change from baseline to 6 months), and glucose metabolism (change from baseline to 6 months).

Example 4

Prospective Assessment of the Effect of Captodiamine on Weight Gain and Body Composition in Adults With Prader-Willi Syndrome The purpose of this study will be to evaluate the effect of captodiamine on the appetite, body weight, body fat and growth hormone level of subjects with PWS. This will be a double blind placebo controlled clinical trial involving a total of 18 young adults aged 18 to 35 years with PWS. Subjects will be selected if they have Prader Willi syndrome previously confirmed by standard genetic testing (the DNA methylation test) or meet the clinical diagnostic criteria as follows: the presence of at least four of the six principal characteristics of PWS syndrome including 1) infantile hypotonia, 2) abnormal pubertal development, 3) obesity after early infancy, 4) dysfunctional central nervous system performance, 5) dysmorphic facial features, and 6) short stature. In addition, they must have one or more of the following characteristics commonly associated with PWS: 1) small hands and feet, 2) skin problems, 3) behavioral problems related to food, and 4) decreased pain sensitivity. Subjects must have a BMI of at least 30 or more. Subjects will be divided in to the two groups of control and intervention, and treated with either placebo (inactive drug), or captodiamine for a total duration of 6 months. Body weight, fat distribution, objective and subjective assessment of the hunger, fasting blood sample for measurement of ghrelin and leptin, serum lipids, IGF-1 (growth hormone related protein), insulin and glucose concentrations will be measured upon enrollment, at 3 months, and at the end of the study. The proportion of body fat to muscle will be determined using a radiological technique, whole body dual-energy x-ray absorptiometry (DEXA) scan, and also by measurement of skin fold thickness, waist and hip circumference at the enrollment prior to the intervention, and at the end of the study.

Example 5

Prospective Assessment of the Effect of Captodiamine on Self-Injurious Behavior in Adults with Prader-Willi Syndrome Prader-Willi syndrome may be characterized by a persistent pattern of self-injurious behavior (SIB), most notably skin picking, that results in frequent medical care and attention. SIB in mental retardation and related developmental disabilities is often monitored by behavioral observation methods. Direct evaluation of skin lesions has been reported to help systematically follow wounds and wound healing. The goal of this study is to characterize SIB in PWS and to evaluate the efficacy of captodiamine versus placebo in attenuating SIB in individuals with PWS.

This will be a double blind placebo controlled clinical trial involving adults aged 18 to 66 years with PWS. Subjects will be selected if they have Prader-Willi syndrome previously confirmed due to deletion of 15 q11-13 or uniparental disomy and are actively engaging skin picking behavior. Participants in the study will be randomized to receive either captodiamine or a placebo for 6 weeks. All participants will be monitored for SIB by observation and photographic recordings of the resultant skin lesions, by reports of group home staff, and by standardized rating measurements of self-injury. At the end of 6 weeks, participants receiving captodiamine will receive decreasing doses of captodiamine; participants receiving placebo will continue to receive the placebo. At week 9, participants previously receiving captodiamine will be given placebo and participants previously receiving placebo will be given captodiamine. After 6 weeks, all participants will be entered into a 4-month open-label extension phase. Safety and efficacy measurements will be assessed during the 15 study visits; in the event of worsening SIB, the blind will be broken by the study's medical oversight physician and, if appropriate, the participant will be placed directly into the 4-month open-label extension phase.

Example 6

Prospective Assessment of the Effect of Captodiamine Therapy on Developmental, Nutritional and Hormonal Regulation of Ghrelin in Children and Young Adults with Prader-Willi Syndrome The purpose of this study is to investigate, over a 6 month period, the effect of captodiamine therapy on food intake, sense of hunger, body weight, body composition, efficiency of burning calories, biomarkers of weight regulation and growth hormone markers in children and young Adults with PWS. This will be a double blind placebo controlled clinical trial involving subjects with a diagnosis of PWS confirmed by chromosome analysis, ages 5 years to 21 years, BMI for age greater-than or equal to 85th percentile, and free T4, thyroid stimulating hormone (TSH) values in the normal range (either endogenous or with thyroxine replacement).

Primary outcome measures are number of participants showing a decrease in fasting total ghrelin from baseline to 6 months of treatment with captodiamine or placebo, number of participants with a decrease in weight from baseline to 6 months of captodiamine or placebo therapy, number of participants with decreased BMI z-score from baseline to 6 months of captodiamine or placebo therapy, number of participants with decreased skin-fold measurements from baseline to 6 months of captodiamine or placebo therapy, number of participants with decrease in hunger and food intake measured by hunger and hyperphagia by questionnaires and parent-reported 72-hour food recall from baseline to 6 months of captodiamine or placebo therapy. Multiple questionnaires consisting of a battery of free text answer questions and food diaries are combined in order to make a behavioral assessment of the participants food state of hunger and food intake. There is no defined scale for this assessment. Each participants' responses and parent responses are combined. Additional primary outcome measures are number of participants with improved insulin regulation from baseline to 6 months of captodiamine or placebo therapy. Insulin regulation will be measured by immunochemiluminescent assay, number of participants with improved adiponectin regulation from baseline to 6 months of of captodiamine or placebo therapy, number of participants with improved Leptin regulation from baseline to 6 months of of captodiamine or placebo therapy, and number of participants with improved Peptide YY (PYY) regulation from baseline to 6 months of captodiamine or placebo therapy. Secondary outcome measures are number of participants with decreased body-composition as measured by air displacement plethysmography (BOD POD® body composition tracking system) from baseline to 6 months of captodiamine or placebo therapy, number of participants with decreased body-composition as measured by dual energy X-ray absorptiometry (DEXA) scan from baseline to 6 months of captodiamine or placebo therapy measured at months 0, 3, and 6, and resting energy expenditure as measured by indirect calorimetry at months 0, 3 and 6.

It should be understood that the examples and embodiments provided herein are exemplary examples embodiments. Those skilled in the art will envision various modifications of the examples and embodiments that are consistent with the scope of the disclosure herein. Such modifications are intended to be encompassed by the claims.

What is claimed is:

1. A method of treating Prader-Willi syndrome comprising administering to a patient in need thereof a pharmaceutical composition comprising an effective amount of from 0.01 mg to 1500 mg captodiamine or a pharmaceutically acceptable salt thereof wherein the composition provides improvement in hypotonia.

2. The method of claim 1, wherein the captodiamine or pharmaceutically acceptable salt thereof is administered as a pharmaceutical composition selected from the group consisting of oral, buccal, sublingual, rectal, topical, intranasal, and parenteral.

3. The method of claim 1, wherein the captodiamine or pharmaceutically acceptable salt thereof is administered in an amount of 1 mg to 500 mg.

4. The method of claim 1, wherein the captodiamine or pharmaceutically acceptable salt thereof is administered in an amount of 50 mg to 250 mg.

5. The method of claim 1, wherein the captodiamine or pharmaceutically acceptable salt thereof is administered in a 24-hour period is between 1 mg and 1500 mg.

6. The method of claim 1, wherein the captodiamine or pharmaceutically acceptable salt thereof is administered from one to four times daily.

7. The method of claim 1, wherein the total amount of captodiamine or a pharmaceutically acceptable salt thereof administered to the patient in a 24-hour period is between 10 mg and 50 mg.

8. The method of claim 1, wherein the daily dosage of the captodiamine or a pharmaceutically acceptable salt thereof is between 10 mg and 20 mg.

9. The method claim 1, wherein the captodiamine or a pharmaceutically acceptable salt thereof is administered twice daily.

10. A method of treating hypotonia in a patient diagnosed with Prader-Willi syndrome comprising administering to the patient a pharmaceutical composition comprising an effective amount of from 0.01 mg to 1500 mg captodiamine or a pharmaceutically acceptable salt thereof.

* * * * *